(12) United States Patent
Schulzki et al.

(10) Patent No.: US 6,629,978 B2
(45) Date of Patent: Oct. 7, 2003

(54) VALGUS ADAPTER

(75) Inventors: Michael J. Schulzki, Boonton, NJ (US); Carlos E. Collazo, Old Greenwich, CT (US); Kenneth Trimmer, Waldwick, NJ (US); Emilio Sanchez, Nutley, NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 228 days.

(21) Appl. No.: 09/841,548

(22) Filed: Apr. 23, 2001

(65) Prior Publication Data
US 2002/0156479 A1 Oct. 24, 2002

(51) Int. Cl.⁷ .................................................. A61F 5/00
(52) U.S. Cl. ........................................................ 606/86
(58) Field of Search ............................. 606/88, 87, 86, 606/53

(56) References Cited

U.S. PATENT DOCUMENTS

| | | | |
|---|---|---|---|
| 4,474,177 A | | 10/1984 | Whiteside |
| 4,487,203 A | | 12/1984 | Androphy |
| 4,567,885 A | | 2/1986 | Androphy |
| 4,653,488 A | * | 3/1987 | Kenna et al. .................. 606/88 |
| 4,722,330 A | | 2/1988 | Russell et al. |
| 4,759,350 A | * | 7/1988 | Dunn et al. .................... 606/82 |
| 5,037,423 A | * | 8/1991 | Kenna ............................ 606/88 |
| 5,053,037 A | | 10/1991 | Lackey |
| 5,417,695 A | | 5/1995 | Axelson, Jr. |
| 5,562,675 A | * | 10/1996 | McNulty et al. ............... 606/96 |
| 5,624,444 A | * | 4/1997 | Wixon et al. ................... 606/88 |
| 5,658,292 A | | 8/1997 | Axelson, Jr. |
| 5,676,668 A | * | 10/1997 | McCue et al. .................. 606/87 |
| 5,683,397 A | * | 11/1997 | Vendrely et al. ............... 606/88 |
| 5,735,856 A | | 4/1998 | McCue et al. |
| 5,860,980 A | * | 1/1999 | Axelson et al. ................ 606/88 |
| 5,911,723 A | * | 6/1999 | Ashby et al. ................... 606/88 |
| 5,916,219 A | * | 6/1999 | Matsuno et al. ............... 606/88 |
| 6,063,091 A | | 5/2000 | Lombardo et al. |
| 6,090,114 A | | 7/2000 | Matsuno et al. |
| 6,096,082 A | * | 8/2000 | Stegmuller et al. ....... 623/20.15 |
| 6,228,091 B1 | | 5/2001 | Lombardo et al. |
| 6,258,095 B1 | * | 7/2001 | Lombardo et al. ............. 606/88 |
| 6,344,043 B1 | | 2/2002 | Pappas |
| 6,423,096 B1 | * | 7/2002 | Musset et al. ............ 623/20.15 |

* cited by examiner

*Primary Examiner*—Eduardo C. Robert
(74) *Attorney, Agent, or Firm*—Lerner, David, Littenberg, Krumholz & Mentlik, LLP (57) ABSTRACT

IM revision tools include a cutting guide having a coupling (preferably a male dovetail coupling), and a plurality of valgus adapters each having a mating (for example, female dovetail) coupling. According to a preferred embodiment of the invention, ten valgus adapters are provided: left and right with offsets of 0 mm, 2 mm, 4 mm, 6 mm, and 8 mm. All but the 0 mm valgus adapters are provided with dual rotational joints which allow a cutting guide to be positioned in both the anterior-posterior direction as well as in the medial-lateral direction. All but the 0 mm valgus adapters are provided with a reverse clock face below the female dovetail coupling. The methods include selecting the appropriate valgus adapter, attaching the valgus adapter to an IM stem and to the cutting guide, and inserting the IM stem into the femoral canal. If 0 mm offset adapter is not chosen, the cutting guide can be orbited 360° to position the cutting guide correctly. When the cutting guide is in position the degree of rotation can be determined by reading the reverse clock face on the valgus adapter. The reverse clock face reading can then be used to adjust the offset of the implant by setting the implant offset to the same setting.

23 Claims, 4 Drawing Sheets

VALGUS ADAPTER

This application is related to co-owned application Ser. No. 09/049,705, now U.S. Pat. No. 6,258,095, entitled "Methods and Tools for Femoral Intermedullary Revision Surgery", filed Mar. 28, 1998, the complete disclosure of which is hereby incorporated herein by reference.

BACKGROUND OF THE INVENTION

1. Field of the Invention

The invention relates to methods and tools used in knee arthroplasty. More particularly, the invention relates to methods and tools typically used in revision surgery where an artificial femoral component is removed and replaced.

2. Brief Description of the Prior Art

Total knee arthroplasty involves the replacement of portions of the patella, femur and tibia with artificial components. In particular, a proximal portion of the tibia and a distal portion of the femur are cut away (resected) and replaced with artificial components.

As used herein, when referring to bones or other body parts, the term "proximal" means closest to the heart and the term "distal" means more distant from the heart. When referring to tools and instruments, the term "proximal" means closest to the practitioner and the term "distal" means distant from the practitioner.

There are several types of knee prostheses known in the art. One type is sometimes referred to as a "resurfacing type". In these prostheses, the articular surface of the distal femur and proximal tibia are "resurfaced" with respective metal and plastic condylar-type articular bearing components. These knee prostheses provide adequate rotational and translational freedom and require minimal bone resection to accommodate the components within the boundaries of the available joint space.

The femoral component is typically a metallic alloy construction (cobalt-chrome alloy or 6A14V titanium alloy) and provides medial and lateral condylar bearing surfaces of multi-radius design of similar shape and geometry as the natural distal femur or femoral-side of the knee joint.

The tibial component usually includes a distal metal base component and a proximal interlocking plastic, e.g. UHM-WPE (ultra high molecular weight polyethylene), component or insert. The plastic tibial plateau bearing surfaces are of concave multi-radius geometry to more or less match the articular geometry of the mating femoral condyles. Both the femoral and tibial components are usually provided with intermedullary (IM) stem options.

After preparing the distal surface of the femur and the proximal surface of the tibia, an opening is made into the medullary canal of the femur, and an opening is made into the medullary canal of tibia. The interior surface and the IM stem of the femoral component are usually covered with a polymeric cement and the IM stem is inserted into the medullary canal of the femur until the interior surface of the femoral component meets the distal surface of the femur. The tibial component is similarly usually cemented to the proximal surface and medullary canal of the tibia.

Occasionally, the components are press fit without the use of cement. The use of cement has advantages and disadvantages. Press fit components rely on bone quality to obtain good fixation. Sometimes it is impossible to obtain good fixation with a press fit component and sometimes a press fit component will fail early because of failure of successful biological ingrowth. Cement assures good fixation but puts strain along the component stem. In addition, as described below, cement complicates the removal of a failed component.

Often, due to normal wear over time, the prosthetic knee must be replaced via a procedure known as revision surgery. When the primary cemented prosthetic is removed, the proximal surface of the tibia and the distal surface of the femur typically exhibit cavernous defects. Absent the use of bone graft, the proximal surface of the tibia and the distal surface of the femur must be carefully resected to remove cavernous defects before a replacement knee can be installed.

In addition, the intermedullary (IM) canals must be broached or reamed to remove any remaining cement or cavernous defects existing in the canals before a replacement knee can be installed. In many instances, the replacement femoral component will be provided with an anterior or posterior stabilizer and an anterior or posterior distal portion of the femur will need to be removed in order to accommodate the stabilizer.

The absence of bony landmarks (removed during primary surgery) and the presence of cavernous defects make extramedullary (EM) alignment of cutting jigs difficult even in cases where the primary prosthetic did not use cement.

The state of the art method for accomplishing revision arthroplasty involves the use of several cutting guides which must be aligned with reference to the IM canal.

After the primary prosthetic is removed, the distal femur is resected with a lateral template. The medullary canal is reamed and the reamer is tapped in place with a mallet. A distal resection guide is attached to the reamer and distal resection is completed via slots in the guide. The distal resection guide is removed from the reamer and another cutting guide is attached to the reamer for A/P and chamfer resections.

The rotational alignment of the femoral component is critical to ensure correct patellar tracking. Since the posterior condyles are no longer present, this cutting guide must be carefully aligned relative to the femoral epicondyles where the collateral ligaments are attached.

After anterior/posterior and chamfer resections are completed, the cutting guide is removed and a fourth cutting guide is attached to the reamer in order to accomplish intercondylar box resection. It will be appreciated that the installation and removal of the several cutting guides makes alignment of the cutting guides more difficult.

Following preparation of the femur, similar procedures are performed on the proximal tibia.

Previously incorporated, co-owned application Ser. No. 09/049,705 discloses IM revision tools including:

(a) reamers with depth markings and/or depth stops;

(b) an impactor-extractor with a distal coupling for attaching to other tools which are inserted into and removed from the IM canal;

(c) a resection guide tower to which a cutting guide is accurately attached and which includes a notch which serves as both a witness mark and a holder for a femoral or tibial collar;

(d) a selection of different sized stems attachable to the guide tower;

(e) a selection of different sized femoral and tibial collars;

(f) a reversible cutting guide with a quick-connect clamp attachable to the guide tower for resecting the distal femur;

(g) a right and left cutting guide with quick-connect clamp attachable to the guide tower for resecting the proximal tibia;

(h) a selection of spacer blocks for measuring the space between the tibia and femur to determine the thickness of the tibial component to be installed;

(i) an all-in-one cutting guide for preparing the femur;

(j) a set of 5 and 10 mm trial wedges;

(k) a trial stem valgus adapter;

(l) femoral sizing indicators which include indications of anterior/posterior offset;

(m) a posterior stabilizer box cutting template which is attachable to the all-in-one cutting guide; and (n) anterior/posterior offset adapters for attaching the femoral component to the IM stem.

The tools are modular and can also be used in primary knee arthroplasty with or without IM fixation.

The methods disclosed in the co-owned application include:

(a) removing the primary femoral component;

(b) reaming an appropriate depth of the femoral IM canal with a reamer of appropriate diameter;

(c) selecting a tool stem (trial stem) of appropriate length and diameter;

(d) attaching the guide tower to the tool stem;

(e) inserting the tool stem into the femoral IM canal;

(f) attaching the impactor/extractor to the proximal end of the tool stem and impacting the stem into the IM canal (or optionally impacting the stem with a mallet);

(g) optionally attaching a stop to the tool stem prior to impacting;

(h) attaching the reversible cutting guide to the tool stem resecting the distal femur;

(i) removing the cutting guide from the tool stem and removing the tool stem with the impactor/extractor;

(j) repeating the procedure with respect to the proximal tibia using one of the left or right tibial cutting guides;

(k) sizing the distal femur and the space between the femur and tibia at flexion and extension;

(l) inserting a tool stem into the femoral IM canal;

(m) attaching an all-in-one cutting guide of appropriate size to the tool stem;

(n) optionally inserting a 5 or 10 mm spacer to the distal side of the cutting guide before attaching to the tool stem;

(o) referencing the rotational alignment of the all-in-one cutting guide to the posterior condyles (if present), or aligning the all-in-one cutting guide parallel to the transepicondylar axis with the aid of a spacer block;

(p) attaching a sizing indicator to the all-in-one cutting guide to confirm the cutting guide size;

(q) inserting pins through the all-in-one cutting guide and into the distal femur;

(r) making the anterior cut of the femur using the all-in-one cutting guide;

(s) optionally attaching a stabilizer with an anterior reference plate which is pinned to the anterior of the femur;

(t) making the chamfer and posterior cuts using the all-in-one cutting guide;

(u) drilling through guides in the all-in-one cutting guide to locate the position of the posterior stabilizer box;

(v) attaching the posterior stabilizer box template to the all-in-one cutting guide; and (w) inserting the posterior stabilizer box chisel through the template to remove bone for the posterior stabilizer box.

The methods and tools of the co-owned application provide accurate location of bone cuts so that the revision prosthetic is correctly oriented relative the IM canal and the bone cuts. However, the ability for the surgeon to locate the all-in-one cutting guide in both the medial-lateral and anterior-posterior directions is not inherent in the co-owned application. Moreover, the cutting guide does not allow for an anterior box cut.

SUMMARY OF THE INVENTION

It is therefore an object of the invention to provide methods and tools for performing IM revision surgery.

It is also an object of the invention to provide tools for IM revision surgery which maintain proper alignment with the IM canal while multiple resection cuts are made.

It is another object of the invention to provide methods for performing IM revision surgery in which a minimum number of tools are used.

It is still another object of the invention to provide methods and tools which enhance the accuracy of Im revision surgery and enhance the stability of the revision implant.

It is yet another object of the invention to provide a cutting guide which is locatable in both the medial-lateral and anterior-posterior directions with infinite degrees of freedom.

It is still another object of the invention to provide a cutting guide which permits an anterior box cut.

In accord with these objects, which will be discussed in detail below, the IM revision tools of the present invention include a cutting guide having a male dovetail coupling, and a plurality of valgus adapters each having a female dovetail coupling. Other coupling means are contemplated by the invention as well, such as a keyed coupling means or indeed any other mechanism which enables the cutting guide to move relative to the femur when secured thereto, for example, via a shaft extending into the medullary canal of the femur.

The cutting guide contemplated by the invention is provided with a plurality of cutting guide surfaces, various scribe lines, and an anterior flange defining a box cut template. According to a preferred embodiment of the invention, ten valgus adapters are provided: left and right with offsets of 0 mm, 2 mm, 4 mm, 6 mm, and 8 mm. All but the 0 mm valgus adapters are provided with dual rotational joints which allow a cutting guide to be positioned in both the anterior-posterior direction as well as in the medial-lateral direction. Furthermore, according to the illustrative embodiment of the invention being set forth herein all but the 0 mm valgus adapters are provided with a reverse clock face below the female dovetail coupling.

One method contemplated by the present invention includes the following steps:

(a) selecting the appropriate valgus adapter;

(b) attaching the valgus adapter to an IM stem and to the cutting guide; and (c) inserting the IM stem into the femoral canal, such that if a 2 mm, 4 mm, 6 mm or 8 mm offset adapter is chosen, the cutting guide can be orbited 360° to position the cutting guide correctly.

Further, a blade runner can be inserted into the slot for the anterior cut to ensure that this cut will not notch the femur.

Still further, according to the invention, the front face of the cutting guide, as well as the scribe lines on the top of the cutting guide, indicate the medial-lateral dimension of the femoral component. This aids the surgeon in the medial-lateral placement of the femoral component.

The internal-external rotation of the femoral component may be determined by one of two methods. By placing the cutting guide on an appropriate spacer block when the knee is in flexion; or by inserting quick release handles into the appropriate holes in the all in one guide and insuring that the handles are parallel to the transepicondylar axis. A scribe on the anterior flange indicates the height of the anterior flange on the femoral component.

Only after the correct position, rotation, and offset have been determined is the cutting guide pinned in place. This can be accomplished with pins on the medial and lateral sides of the cutting guide and on the anterior flange.

When the cutting guide contemplated by the invention is in position, the degree of offset adapter rotation can be determined by reading the reverse clock face on the valgus adapter. The reverse clock face reading can then be used to adjust the offset of the implant by setting the implant offset to the same setting.

The anterior cut, anterior chamfer, and posterior chamfer cuts can then be made in the appropriate slots. The posterior neutral cut is a surface cut on the bottom face. If necessary, the 5 mm and 10 mm posterior augment cuts are made through the appropriate slots.

The preparation for the intercondylar box can be accomplished in two different directions. The surgeon has the option of utilizing a narrow saw blade and using the window cut out on the anterior flange to guide the cuts. This is the anterior approach. The surgeon can also utilize the sides of the dovetail coupling window to guide a narrow saw blade in the preparation of the intercondylar box. This is the distal approach.

The cutting guide also has adaptability via modular fixation pins that attach to the cutting guide via screw threads. If distal augmentation is required, the cutting guide is designed to accept trial spacers to stabilize the femoral preparation via holes in its proximal surface.

The methods and tools of the invention provide accurate location of bone cuts so that the revision prosthetic is correctly oriented relative the IM canal and the bone cuts. Additional objects and advantages of the invention will become apparent to those skilled in the art upon reference to the detailed description taken in conjunction with the provided figures.

DETAILED DESCRIPTION

Figure 1:
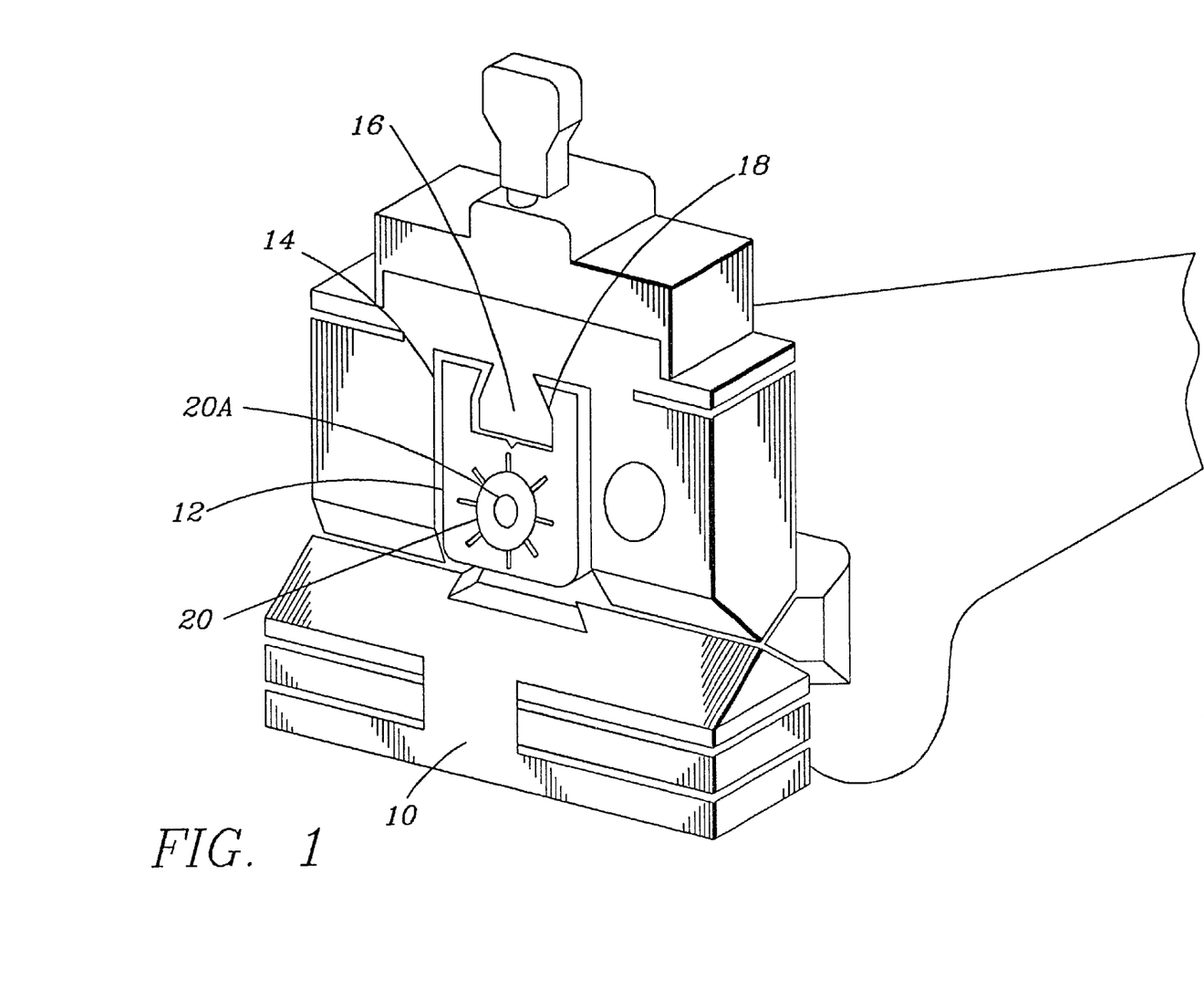
FIG. 1 is a perspective view of tools according to the invention attached to a distal femur.

FIG. 1 illustrates a cutting guide 10 and valgus adapter 12 installed on a distal femur. As will be described in more detail below with reference to FIGS. 5–7, the cutting guide 10 has a plurality of guiding surfaces for guiding anterior, posterior and chamfer cuts.

According to one aspect of the invention, the cutting guide 10 has a central window 14 within which a male dovetail coupling 16 extends and the valgus adapter 12 is provided with a mating female dovetail coupling 18.

According to another aspect of a preferred, non-limiting embodiment of the invention, ten valgus adapters are provided: left and right with offsets of 0 mm, 2 mm, 4 mm, 6 mm, and 8 mm. All but the 0 mm valgus adapters are provided with dual rotational joints (described in more detail below with reference to FIGS. 2–4) and a reverse clock face 20 below the female dovetail coupling 18.

Figure 2:
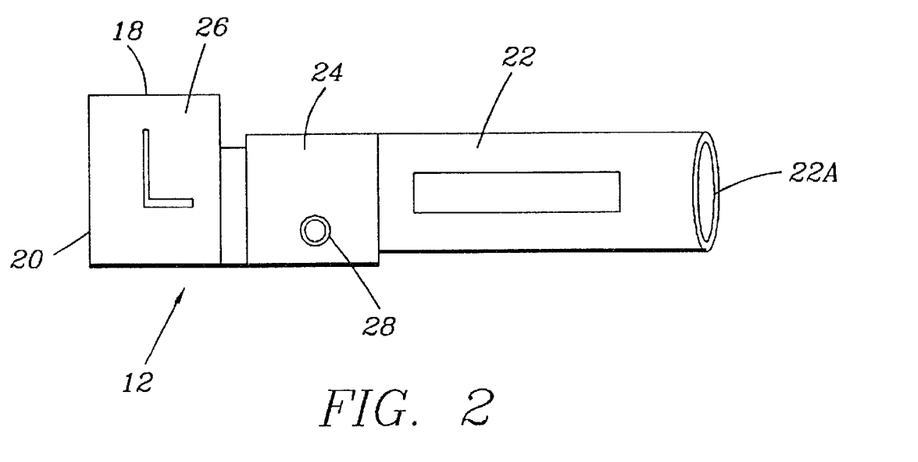
FIG. 2 is a side elevation view of a valgus adapter according to the invention.
Figure 3:
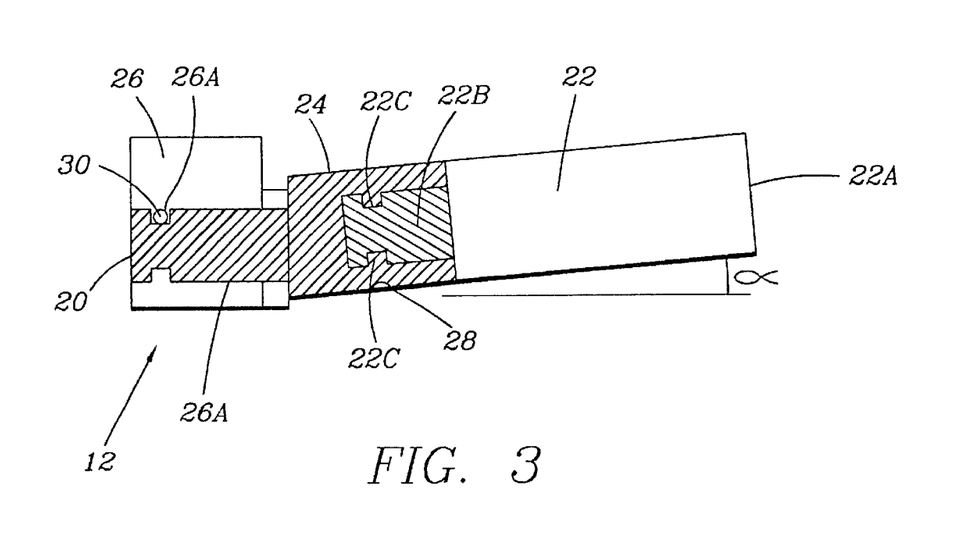
FIG. 3 is a top view in partial section illustrating one embodiment of a valgus adapter according to the invention.
Figure 4:
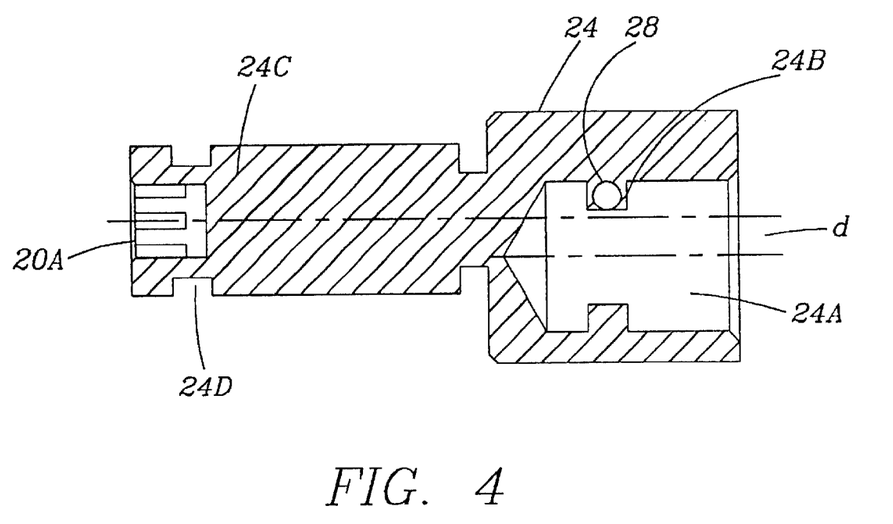
FIG. 4 is a sectional view of a component of the valgus adapter of FIG. 3.

Referring now to FIGS. 2–4, all but the 0 mm valgus adapters are made, according to an illustrative preferred embodiment of the invention, of five components: (a) an adapter shaft 22; (b) an offset adapter 24,; (c) an adapter footing 26 (d) and two pins 28, 30.

The adapter shaft 22 has a threaded coupling 22a and a spindle 22b having a circumferential groove 22c.

The offset adapter 24 has a spindle receptacle 24a, an orthogonal pin hole 24b, and a spindle 24c with a circumferential groove 24d. The axis of the spindle 24c is offset from the axis of the spindle receptacle 24a by an offset amount "d" which may be 2 mm, 4 mm, 6 mm, or 8 mm.

According to the preferred embodiment of the invention, the end of the spindle 24c is provided with a clock pointer 20a which is seen best in FIG. 1. The footing 26 has a spindle receiving throughbore 26a and an orthogonal pin hole 26b.

The pieces are assembled by inserting the spindle 22b into the spindle receptacle 24a and securing it with pin 28 which is inserted through pin hole 24b and engages the groove 22c in the spindle 22b. The spindle 24c is inserted in the throughbore 26a and is secured with pin 30 which is inserted in pin hole 26b and engages the groove 24d.

After assembly, the pins are preferably burnished. As seen best in FIG. 3, the assembled valgus adapter provides a valgus angle [alpha] which is preferably 6° and which is provided by the angle of the throughbore 26a. The 0 mm offset valgus adapter provides the same 6° angle, but is not offset and has no moving parts.

Figure 5:
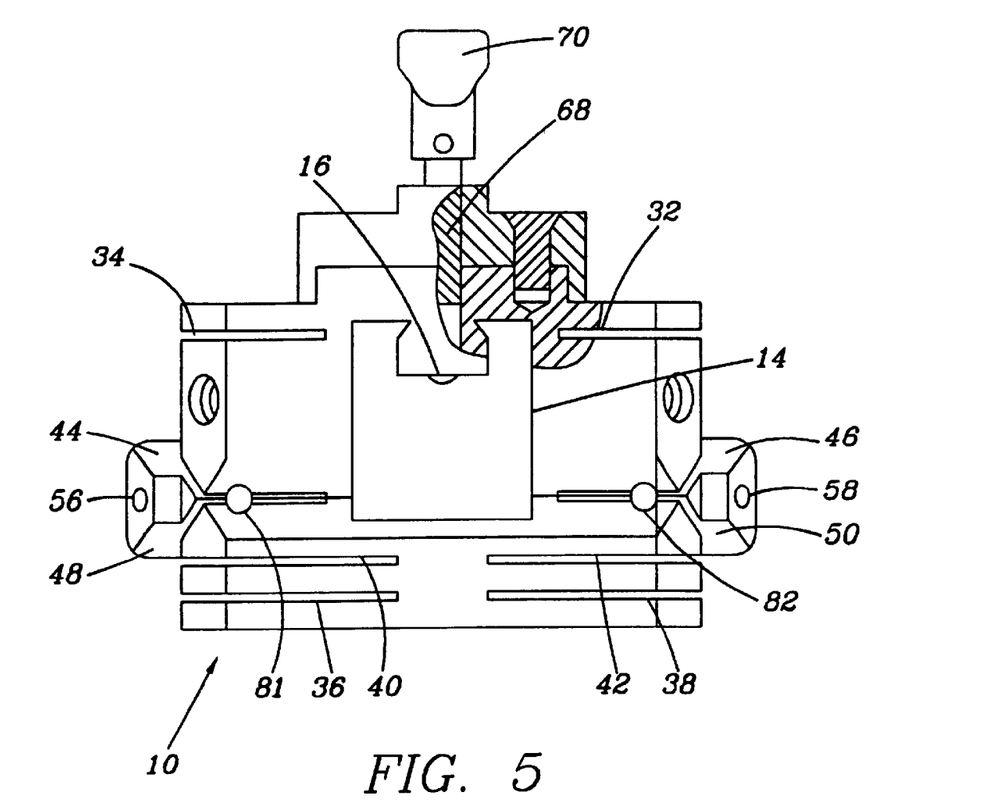
FIG. 5 is a front elevation view in partial section of a cutting guide according to the invention.
Figure 6:
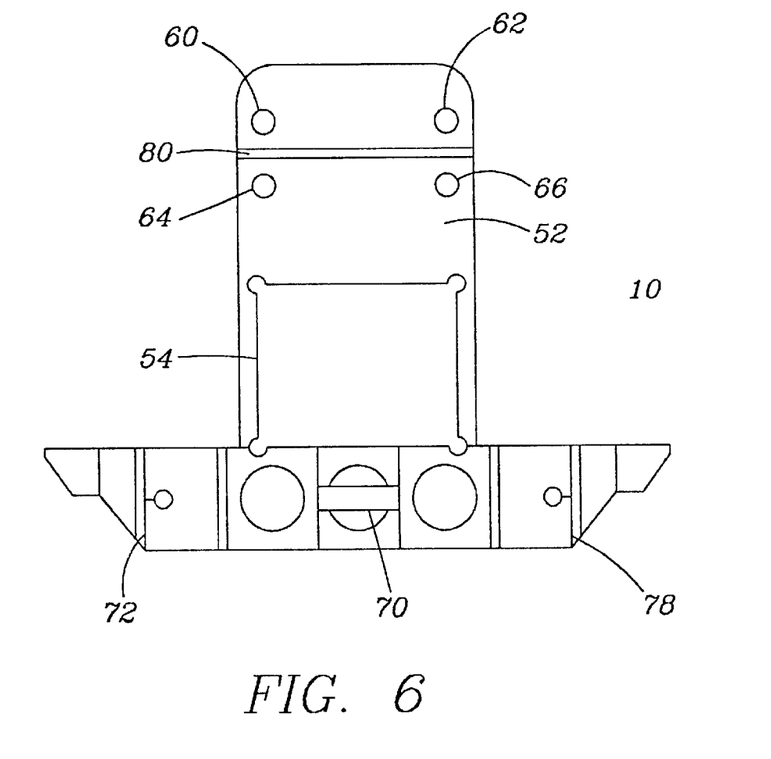
FIG. 6 is a top plan view of the cutting guide of FIG. 5.
Figure 7:
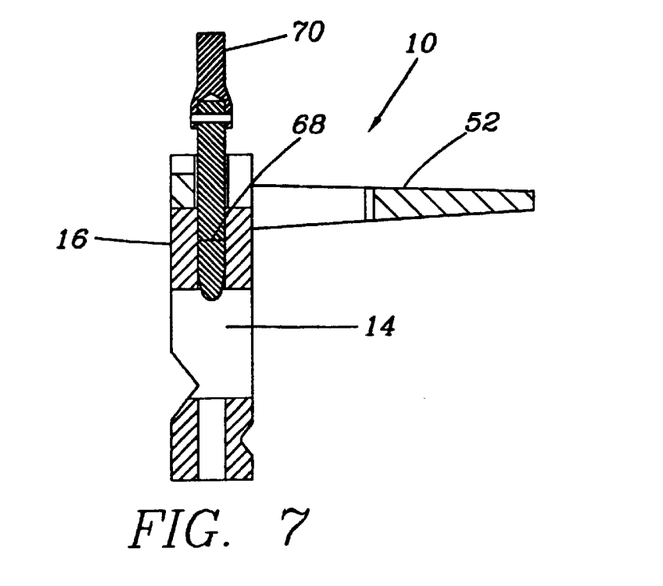
FIG. 7 is a side elevation view in partial section of the cutting guide of FIG. 5.

Referring now to FIGS. 5–7, as mentioned above, the cutting guide 10 includes a central window 14 within which a male dovetail coupling 16 is disposed. In addition, the cutting guide 10 includes anterior cutting guide slots 32, 34, posterior cutting guide slots 36, 38, 40, 42, and chamfer cutting guide slots 44, 46, 48, 50. An anterior flange 52 extends back from the face of the cutting guide and defines an anterior box cut template 54.

The cutting guide 10 has medial and lateral anchoring bores 56, 58 as well as anterior anchoring bores 60, 62, 64, 66. According to the presently preferred embodiment, the male dovetail coupling 16 is provided with a setscrew 68 with a thumb drive 70 so that the cutting guide may be securely attached to the valgus adapter. According to the presently preferred embodiment, the top of the cutting guide is provided with medial and lateral scribe lines 72, 78 and the anterior flange 52 is provided with a scribe line 80 to aid in positioning.

From the foregoing, those skilled in the art will appreciate that the tools described above are best used in conjunction with other tools described in the previously incorporated application. For example, the reamers, broachers, cutting blades, affixation pins, and IM rods described in the prior application will be useful in using the tools described herein.

Those skilled in the art will also appreciate that portions of the methods described in the prior application will be useful in conjunction with the methods taught herein. For example, the previous methods for removing a prosthetic to be replaced and for installing a new prosthetic may be used together with the methods taught herein.

In summary, i.e. without describing all of the method steps already known in the art, the methods of the present invention include:

(a) selecting the appropriate valgus adapter 12;

(b) attaching the valgus adapter to an IM stem (not shown) and to the cutting guide 10; and (c) inserting the IM stem into the femoral canal. If a 2 mm, 4 mm, 6 mm or 8 mm offset adapter is chosen, the cutting guide can be orbited 360° to position the cutting guide correctly.

A blade runner (not shown) can be inserted into the slots 32, 34 for the anterior cut to ensure that this cut will not notch the femur.

The front face of the cutting guide 10, as well as the scribe lines 72, 78 on the top of the cutting guide, indicate the medial-lateral dimension of the femoral component. This aids the surgeon in the medial-lateral placement of the femoral component.

The internal-external rotation of the femoral component may be determined by one of two methods. By placing the cutting guide on an appropriate spacer block when the knee is in flexion; or by inserting quick release handles into the appropriate holes in the all in one guide and insuring that the handles are parallel to the transepicondylar axis. The scribe 80 on the anterior flange 52 indicates the height of the anterior flange on the femoral component. Only after the correct position, rotation, and offset have been determined is the cutting guide pinned in place. This is accomplished with pins through holes 56, 58 on the medial and lateral sides of the cutting guide and 60, 62, 64, 66 on the anterior flange 52.

When the cutting guide is in position the degree of offset adapter rotation can be determined by reading the reverse clock face 20 on the valgus adapter. The reverse clock face reading can then be used to adjust the offset of the implant by setting the implant offset to the same setting. For reasons apparent to those skilled in the art, the clock face on the implant is a mirror image of the clock face on the valgus adapter.

The anterior cut, anterior chamfer, and posterior chamfer cuts are made in the appropriate slots, i.e. 32, 34, 44, 46, 48, 50. The posterior neutral cut is a surface cut on the bottom face of the cutting guide. If necessary, the 5 mm and 10 mm posterior augment cuts are made through the slots 36, 38, 40, 42.

The preparation for the intercondylar box can be accomplished in two different directions. The surgeon has the option of utilizing a narrow saw blade and using the template 54 on the anterior flange to guide the cuts. This is the anterior approach. The surgeon can also utilize the sides of the dovetail coupling window 14 to guide a narrow saw blade in the preparation of the intercondylar box. This is the distal approach.

The cutting guide also has adaptability via modular fixation pins that attach to the cutting guide via screw threads. If distal augmentation is required, the cutting guide is designed to accept trial spacers to stabilize the femoral preparation via holes in its proximal surface (holes 81 and 82 as seen in FIG. 5).

There have been described and illustrated herein methods and tools for IM revision surgery. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. A valgus adapter for use with a cutting guide having a first coupling, said valgus adapter comprising:

(a) an adapter shaft coupled to (b) an offset adapter; and (c) an adapter footing coupled to said offset adapter opposite said adapter shaft, said adapter footing having a second coupling adapted to mate with said first coupling; and said adapter shaft forming a valgus angle with said second coupling.

2. A valgus adapter according to claim 1 wherein said first coupling is a dovetail coupling and said second coupling is a dovetail coupling adapted to mate with said first coupling.

3. A valgus adapter according to claim 2 wherein said adapter shaft has a rod coupling for coupling it to an IM rod.

4. A valgus adapter according to claim 3 wherein said rod coupling is a threaded coupling.

5. A valgus adapter according to claim 3 wherein said valgus angle is 6°.

6. The valgus adapter according to claim 2 wherein said valgus angle is 6°.

7. The valgus adapter according to claim 1, wherein said valgus angle is 6°.

8. The valgus adapter according to claim 1 wherein said offset adapter comprises a spindle having a spindle axis, and a spindle receptacle having a receptacle axis, wherein said spindle axis is oriented parallel to said receptacle axis, and wherein said spindle is adapted to mate with said adapter footing, and said spindle receptacle is adapted to mate with said adapter shaft.

9. The valgus adapter according to claim 8 wherein said spindle axis is set apart from said receptacle axis by an offset.

10. The valgus adapter according to claim 9 wherein said offset ranges from 1 to 8 millimeters.

11. A valgus adapter for use with a cutting guide, said valgus adapter comprising:

(a) an adapter shaft;

(b) an offset adapter rotatably coupled to said adapter shaft; and (c) an adapter footing rotatably coupled to said offset adapter, said adapter footing having a coupling for mating with said cutting guide such that said adapter footing is free to rotate in an orbit about said adapter shaft, and said adapter shaft forming a valgus angle with said coupling.

12. A valgus adapter according to claim 11 further comprising indicia on one of said adapter footing and said offset adapter for indicating the angular position of said adapter footing relative to said offset adapter.

13. A valgus adapter according to claim 12 wherein said indicia includes a reverse clock face on said adapter footing and a pointer on said offset adapter.

14. A valgus adapter according to claim 11 further comprising a first retaining pin, wherein said adapter shaft has a first spindle with a first circumferential groove, said offset adapter has a spindle bore and a first orthogonal pin hole, and said first spindle is rotatably secured in said spindle bore by said first retaining pin in said first orthogonal pin hole.

15. A valgus adapter according to claim 14 further comprising second retaining pin, wherein said offset adapter has a second spindle with a second circumferential groove, said adapter footing has a spindle throughbore and a second orthogonal pin hole, and said second spindle is rotatably secured in said spindle throughbore by said second retaining pin in said second orthogonal pin hole.

16. A valgus adapter according to claim 15 wherein said second spindle has first indicia on its end, and said adapter footing has second indicia surrounding said spindle throughbore.

17. A valgus adapter according to claim 11 wherein said adapter shaft has a rod coupling for coupling it to an IM rod.

18. A valgus adapter according to claim 17 wherein said rod coupling is a threaded coupling.

19. A valgus adapter according to claim 17 wherein said valgus angle is 6°.

20. The valgus adapter according to claim 11 where said valgus angle is 6°.

21. The valgus adapter according to claim 11 wherein said offset adapter comprises a spindle having a spindle axis, and a spindle receptacle having a receptacle axis, wherein said spindle axis is oriented parallel to said receptacle axis, and wherein said spindle is adapted to mate with said adapter footing, and said spindle receptacle is adapted to mate with said adapter shaft.

22. The valgus adapter according to claim 21 wherein said spindle axis is set apart from said receptacle axis by an offset.

23. The valgus adapter according to claim 22 wherein said offset ranges from 1 to 8 millimeters.

* * * * *

UNITED STATES PATENT AND TRADEMARK OFFICE
CERTIFICATE OF CORRECTION

PATENT NO. : 6,629,978 B2  
DATED : October 7, 2003  
INVENTOR(S) : Michael J. Schulzki et al.

It is certified that error appears in the above-identified patent and that said Letters Patent is hereby corrected as shown below:

<u>Column 4,</u>
Line 26, "Im" should read -- IM --.

Signed and Sealed this

Twenty-third Day of December, 2003

JAMES E. ROGAN
*Director of the United States Patent and Trademark Office*